United States Patent [19]

Chung

[11] Patent Number: 5,599,553
[45] Date of Patent: Feb. 4, 1997

[54] LOCAL DRUG DELIVERY FILM FOR PERIODONTAL TREATMENT

[75] Inventor: Chong P. Chung, Seoul, Rep. of Korea

[73] Assignee: Dong Kook Pharmaceutical Co., Ltd., Seoul, Rep. of Korea

[21] Appl. No.: 392,925

[22] PCT Filed: Dec. 9, 1992

[86] PCT No.: PCT/KR92/00071

§ 371 Date: Feb. 28, 1995

§ 102(e) Date: Feb. 28, 1995

[87] PCT Pub. No.: WO94/05266

PCT Pub. Date: Mar. 17, 1994

[30] Foreign Application Priority Data

Sep. 1, 1992 [KR] Rep. of Korea ............... 1992-15831

[51] Int. Cl.$^6$ .................. A61K 6/00; A61K 9/70
[52] U.S. Cl. ................ 424/435; 424/444; 523/115
[58] Field of Search ................. 424/435, 444; 514/900, 902; 523/115

[56] References Cited

U.S. PATENT DOCUMENTS

| | | | |
|---|---|---|---|
| 4,764,377 | 8/1988 | Goodson | 424/435 |
| 4,892,736 | 1/1990 | Goodson | 424/435 |
| 4,933,182 | 6/1990 | Higashi et al. | 424/435 |
| 4,961,707 | 10/1990 | Magnusson et al. | 433/215 |
| 5,160,737 | 11/1992 | Friedman et al. | 424/401 |
| 5,250,584 | 10/1993 | Ikada et al. | 523/114 |

*Primary Examiner*—Melvyn I. Marquis
*Assistant Examiner*—Robert H. Harrison
*Attorney, Agent, or Firm*— Morgan & Finnegan, LLP

[57] ABSTRACT

The present invention provides a local drug delivery film, which is characterized by comprising, as release control component, polymer mixture consistiong of polycaprolactone having molecular weight of 30,000–60,000 and polycaprolactone having molecular weight less than 1,000 in a ratio of 1:1–4:1, and as active component, periodontal therapeutic agent. The present local drug delivery film is prepared by admixing homogeneously active component with melted polymer mixture and pressing into film. And the present drug delivery film has excellent sustained release pattern and excellent treatment effect in oral disease with release amount 1.7 mg. which is 0.12% of prescription amount, 1400 mg. for adults during 7 days and provides the application stability into human body.

11 Claims, 12 Drawing Sheets

○ Polycaprolactone I 100%
● Polycaprolactone I : Polycaprolactone II = 3 : 1
▽ Polycaprolactone I : Polycaprolactone II = 2 : 1
▼ Polycaprolactone I : Polycaprolactone II = 1.5 : 1

○ Polycaprolactone I  100%
● Polycaprolactone I : Polycaprolactone II = 3 : 1
▽ Polycaprolactone I : Polycaprolactone II = 2 : 1
▼ Polycaprolactone I : Polycaprolactone II = 1.5 : 1

○: Content of minocycline, 23%
●: Content of minocycline, 30%
▽: Content of minocycline, 40%

○: Thickness of film, 200 μm
●: Thickness of film, 250 μm
▽: Thickness of film, 350 μm ○ : Concentration of minocycline in periodontal pocket, μg/ml ● : In vitro release rate, μg/cm²/hr

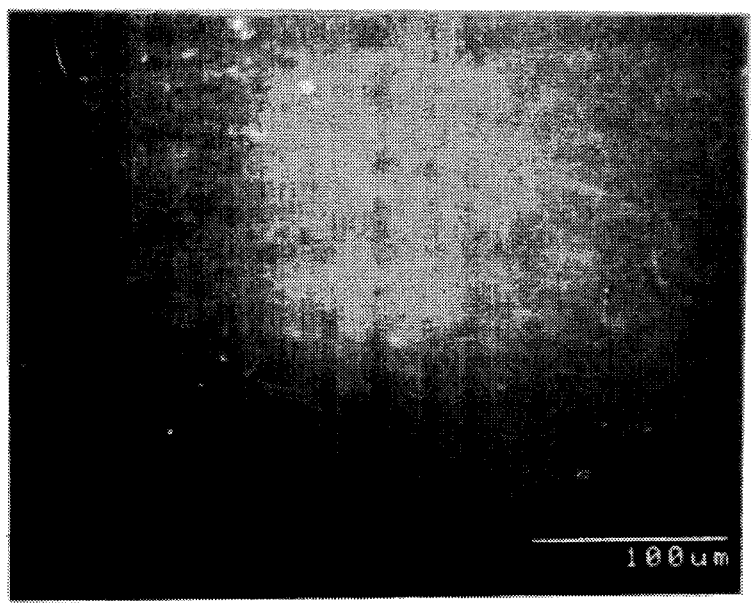
FIG. IIA
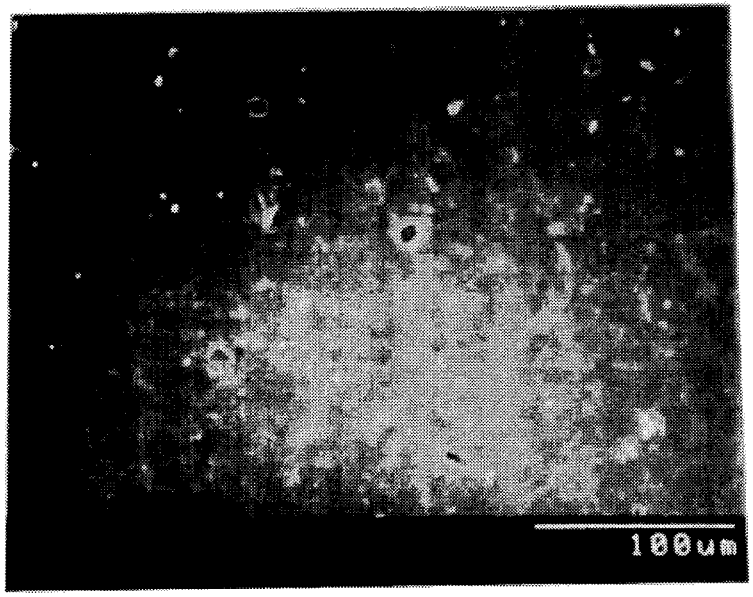
FIG. IIB

LOCAL DRUG DELIVERY FILM FOR PERIODONTAL TREATMENT

BACKGROUND OF THE INVENTION

1. Field of the Invention

The present invention relates to a local drug delivery for periodontal disease treatment and, in detail, it relates to a local drug delivery film for periodontal treatment containing a periodontal therapeutic agent for an active component and a mixture of two kinds of polycaprolactone having different molecular weights, which has excellent sustained releasing properties with effective concentration for periodontal treatment, can be prepared easily by melt casting and has a excellent stability in a human gingival fibroblast.

2. Description of the Prior Art

Recently, concerns about the development of new kinds of drug have been emphasized but the cost is prohibitive. Alternatively, many researches relating to the development of various kinds of local drug delivery to increase the effect of a prescription of a conventional active component show a tendency to increase. Particularly, there were many suggestions in the field of treatment for diabetes, hypertension, cancer and periodontal disease.

Since tetracycline-filled cellulose acetate hollow fiber was proposed at first by Goodson et al. ("Periodontal therapy by local delivery of tetracycline" J. Clin. Periodontal., 6: 83, 1979), many kinds of release control systems were studied using dialysis tube, polyethylene, polypropylene, ethylene vinyl acetate, polycaprolactone, collagen, acrylic strip, etc. Particularly, in the case of the cellulose acetate as release control material, release controlled drug delivery was studied in the form of hollow fiber or film.

But, concerning the results of these studies, in the case of tetracycline-filled hollow fiber prepared by Goodson et al., 95% of tetracycline was released within 2 hours, the half life of release ($t_{1/2}$rel) was about 0.5 hour and the concentration of tetracycline in gingival fibroblast was 15 µg/ml after 24 hours.

This non-sustained release was also shown in conventional local drug delivery using dialysis tube, polyethylene, polypropylene, polyurethane, polycaprolactone and cellulose acetate, and most drug contained in such preparations was released within 24 hours.

In case of ethylene vinyl acetate fiber, sustained release pattern was shown for 9 days, but initial release concentration was 650 µg/ml and the half life of release was 13 hours. That is, even if the effect of the drug itself came out, there was a tendency that the durability of the effect of drug was on the decrease.

Also, jelly-type delivery system containing 2% of minocycline was studied in Japan, in which the concentration of minocycline in gingival fluid decreased rapidly till 7 hours after prescription and was 3.4 µg/ml after 3 days and 0.1 µg/ml after 7 days. That is, there was the effect of drug itself, but there was a tendency that durability of the effect of drug was on the decrease.

To solve these problems, the present inventor developed a local drug delivery film which increased the durability of the effect of drug by mixing of the tetracycline as an active component and biodegradable polycaprolactone as a release control component, and filed with Korean patent application No. 1990-4398. This film is prepared by solution casting including dissolving a polymer in a solvent, adding an active component or its suspension into the polymer solution, mixing together homogeneously and volatilizing the solvent. Accordingly, there are several problems, that is, the potential existence of toxic solvent residue and non-uniform dispersion of active components in the film due to irregular volatilization of solvent giving rise to the unsteady pattern of drug release. Therefore there is room for improvement.

SUMMARY OF THE INVENTION

The present invention has been made in view of above-described problems of the prior art and an object of the invention is to provide film-type local drug delivery which release a periodontal therapeutic agent continuously to keep the optimum concentration to sterilize bacilli in gingival fluid, maximizes the treatment effect, can be applied in human body safely, and can be prepared easily.

According to the present invention, the object mentioned above can be accomplished by providing a local drug delivery film comprising a specific mixture of two kinds of polycaprolactone having different molecular weights as a release control component and a periodontal therapeutic agent as an active component.

BRIEF DESCRIPTION OF THE DRAWINGS

This and other objects, features and advantages of the invention will become more apparent upon a reading of the following detailed description and drawings, in which:

FIGS. 11A and 11B are scanning electron microscope photographs representing before release and after relese for 7 days of minocycline of the strip-type local drug delivery film prepared from Example 2 according to the present invention respectively.

DETAILED DESCRIPTION OF THE PREFERRED EMBODIMENTS

The present invention provides a local drug delivery film for periodontal treatment which is characterized by:

(a) as release control component, 60%–90% by weight of polymer mixture of polycaprolactone having number average molecular weight of in a range of from 30,000 to 60,000 (hereinafter referred to polycaprolactone I) and polycaprolactone having number average molecular weight less than 1,000 (hereinafter referred to as polycaprolactone II) in which the weight ratio of the polycaprolactone I to polycaprolactone II is from 1:1 to 4:1, and (b) as active component, 10%–40% by weight of periodontal therapeutic agent.

Preferably, the polymer mixture which used as release control component is a mixture of polycaprolactone I having number average molecular weight of from 30,000 to 60,000 and polycaprolactone II having number average molecular weight of from 860 to 1,000. The ratio of polycaprolactone I to polycaprolactone II in the mixture is in a range of 1:1–4:1, preperably 1.5:1–3:1.

If the ratio of polycaprolactone I to polycaprolactone II is less than 1:1, the flexibility of the film becomes too large, and if more than 4:1, the flexibility of the film becomes too small.

The preferable examples of periodontal therapeutic agent as active component (b) are at least one kind of antibiotics such as minocycline, tetracycline, doxycycline, chlorohexidine, clindamycin, orfloxacin, metronidazole, tinidazole and ketoconazole. It would be understood that the active component (b) may further contain dental drugs such as antiphlogistic analgesics other than the antibiotic.

The content of active component (b) is in the range of from 10% to 40% by weight, preferably from 20% to 35% by weight of the total amount of release control component and active component (a+b).

The local drug delivery according to the present invention is preferably prepared by melting and mixing homogeneously the polycaprlacton I and II, admixing homogeneously the periodontal therapeutic agent with thus-obtained polycaprolactone mixture melt, and then film-fabricating into a desired shape. For the film fabrication melt pressing or melt extrusion can be used.

Preferably, the local drug delivery of the present invention is fabricated into film having a thickness in a range of from 100 μm to 400 μm, especially from 200 μm to 350 μm. The thickness of film depends on the content of the active component and relates to the duration of active component release. That is, if the content of the active component is constant, the release period of the active component decreases with decreasing thickness of film and the release period increases with increasing thickness of film. Accordingly, to achieve the sustained release of active component with effective concentration for periodontal treatment, control of the thickness of film is necessary.

Figure 1:
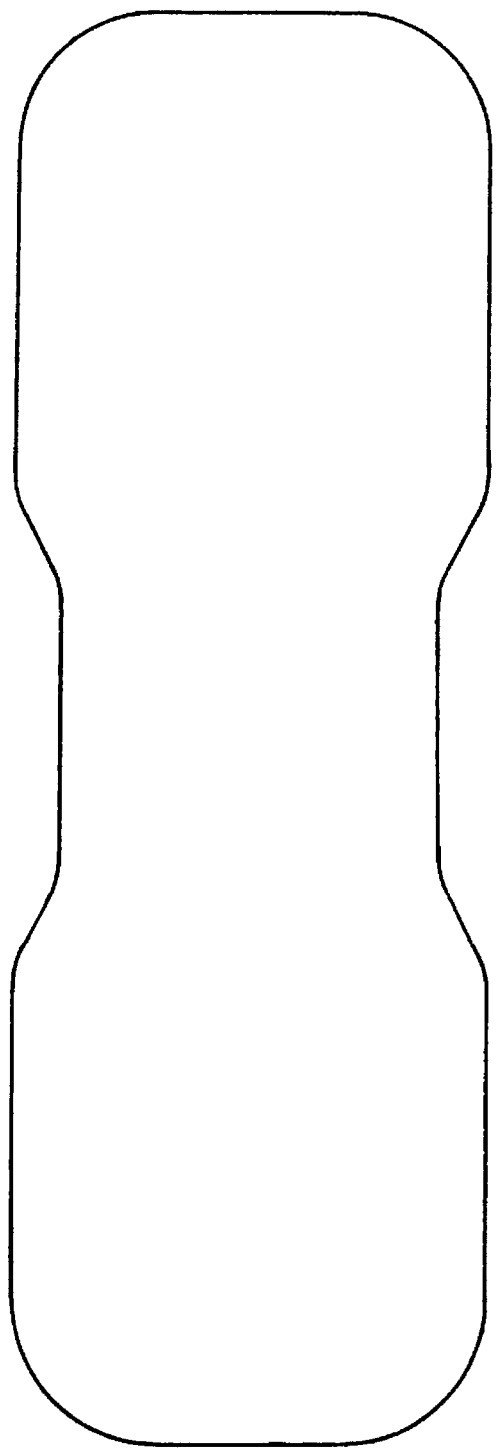
FIG. 1 is a enlarged top view of the strip-type local drug delivery prepared according to an embodiment of present invention.

Preferably, the film has suitable form for insertion into the application position easily and for retention there for a long period of time. For example, a strip-type film having rounded corners and sloped middle portion as shown in FIG. 1 can be easily inserted into the periodontal pocket and can be attached for a long time.

The present invention will now be further described by referring to the following examples. The following Examples and Comparative Examples illustrate the preparation of local drug delivery for periodontal treatment.

1. PREPARATION OF LOCAL DRUG DELIVERY

EXAMPLES 1 TO 6

The strip-type local drug delivery was prepared by undermentioned process.

Pellet-type polycaprolactone I having number average molecular weight of 60,000 and paste-type polycaprolactone II having number average molecular weight of 860 was mixed evenly by mixer at 80° C. for 40 mins.

Thus-obtained polymer melt and minocycline HCl (hereinafter abbreviated to MC) were mixed evenly by mixer at 80° C. for 2 hours to get a homegeneous mixture. Thus-obtained mixture was pressed by press into films having each of thickness 200 μm, 250 μm, 300 μm, and 350 μm respectively.

Each film was cut into strips having the shape of which size was 6.5 mm in length×2.5 mm in breadth and four corners were rounded off and middle part became narrow to insert easily into the periodontal pocket (refer to FIG. 1).

The mixer used was cam-type plasti-corder treated with computer and made by Brabender Co., Ltd. (Germany).

The minocycline HCl used was a fine pariticle having diameter less than 74 μm which was prepared by pulverizing with ball-mill and filtering with KP(Korean Pharmacopeia) sieve number 200.

The foregoing procedure was repeated with the materials and proportions as summarized in Table 1.

COMPARATIVE EXAMPLE 1

The procedure of Example 1 was repeated using only pellet-type polycaprolactone I as polymer.

COMPARATIVE EXAMPLE 2 AND 3

The local drug delivery strips were prepared according to the Example 3 except that the contents of minocycline are 40% and 30% by weight respectively.

TABLE 1

|  | content of MC (wt %) | content of polymer (wt %) | PCL I*: PCL II* | thickness of strip (μm) |
| --- | --- | --- | --- | --- |
| Example 1 | 23 | 77 | 3:1 | 200 |
| Example 2 | 23 | 77 | 2:1 | 200 |
| Example 3 | 23 | 77 | 1.5:1 | 200 |
| Example 4 | 30 | 70 | 1.5:1 | 250 |
| Example 5 | 30 | 70 | 1.5:1 | 350 |
| Example 6 | 30 | 70 | 1.5:1 | 300 |

TABLE 1-continued

|  | content of MC (wt %) | content of polymer (wt %) | PCL I*: PCL II* | thickness of strip (μm) |
|---|---|---|---|---|
| Comparative Example 1 | 23 | 77 | 1:0 | 200 |
| Comparative Example 2 | 40 | 60 | 1.5:1 | 200 |
| Comparative Example 3 | 30 | 70 | 1.5:1 | 200 |

*PCL I: pellet-type polycaprolactone, *PCL II: paste-type polycaprolactone

The local drug delivery film prepared according to the present invention has the advantage of above mentioned for periodontal treatment, At first, the minimal inhibitory concentration (hereinafter it is abbreviated to MIC) of minocycline for bacilli, especially *Antinobacillus actinomycetemcomitans* as main bacillus and the minimum period to optimum treatment effect with MIC were examined. In the susceptibility test of antibiotics to bacilli in mouth, 98% in the 139 kinds of tested bacilli showed the susceptibility and *Actinobacillus actinomycetemcomitans* showed the susceptibility at the concentration of minocycline less than 2–4 μg/ml. From this result, because the break point of minocycline concentration to periodontal treatment was from 2 μg/ml to 4 μg/ml, it was established as theoretical standard that local drug delivery for periodontal treatment should maintain at least 4 μg/ml of the concentration of minocycline in the gingival pocket. Also, it was reported by Goodson et al. that the concentration more than MIC has to be sustained to inhibit growth of periodontal bacillus for at least 48 hours, especially at least 10 days for optimum treatment effect. Accordingly, local drug delivery should sustain the concentration of minocycine in the periodontal pocket at least 4 μg/ml for at least 48 hours, and especially more than 10 days to optimize treatment effect. So the present local drug delivery was examined to learn if it coincided with the standard or not.

Second, in vivo kinetic study was carried out to examine whether minocycline in the local drug delivery is released to sustain the concentration of minocycline more than MIC without cell cytotoxicity.

As a result of above examinations, the local drug delivery satisfied above two conditions in vivo kinetic study.

Release Kinetic Study of Local Drug Delivery

Release kinetic study of strip-type local drug delivery obtained from the Examples 1 to 6 and Comparative examples 1 to 3 was, designed according to Film Theory of Dissolution and the content of theory is as follows:

Dissolution rate is directly proportional to the solubility of drug in receptor solution and dissolution rate after time t is defined as follow:

$$dC/dt = K \cdot x \, (Cs-Ct)$$

Where
dC/dt is dissolution rate,
K is dissolution constant,
Cs is concentration of saturated solution, and
Ct is solution concentration after time t.

Since it is assumed that the liquid is motionless, a saturated solution(Cs) that is called diffusion layer is formed at the solid-liquid interface and the concentration decreases with the growing distance from the interface, reaching concentration(Cb) in the surrounding liquid. The dissolution constant K can be represented as $D/(V \times h)$ and dissolution rate after time t can be represented as following equation as suggested by Nernst and Brunner.

$$dC/dt = (D \times S/h \times V)(Cs-Cb)$$

Where, D is diffusion coefficient, V is solution volume layer, h is thickness of diffusion layer, S is area from which a substance is dissolved, and Cb is concentration of surrounding solution.

In this equation, dC/dt is intrinsic dissolution rate represented as mg/cm$^2$/min under standardized conditions.

If the surrounding liquid is set in motion by either turbulent (by using shaker) or laminar flow (by using flow cell), the dissolved molecules will move more quickly into the surrounding liquid. In such a case the solution is homogeneously mixed all the time. At this time, dC/dt can be simplified as follows:

$$dC/dt = K \times S \times Cs$$

That is, dissolution rate is proportional to dissolution constant, solid surface area and solubility of a drug.

Because dissolution rate is proportional to the concentration difference (Cs–Cb) during liberation, dissolution rate is the greatest at the beginning when Cb=0(zero). So if Cb is large, the rate of dissolution is not constant during the dissolution test because Cb effects on dissolution rate.

As long as the concentration Cb in the solution is below 10% of the saturated solution concentration Cs, the rate of dissolution is constant and this condition is very important for in vitro test and is called as "Perfect Sink Condition".

In the release kinetic study of the present invention, the solubility of minocycline was 2.43 g in the receptor solution as shown in Table 2. That is, because the solubility of minocycline hydrochloride was 243 mg in 10 ml of solution, even if all 1.7 mg contained in strip-type local drug delivery film was released at initial of the test, it was only 0.78% of saturated solubility (Cs) and it satisfied the Perfect Sink Condition.

Also, dissolution rate is calculated as intrinsic dissolution rate or fraction release (%) per unit surface area of this system. Therefore, the test should be done with the strip having constant surface area to eliminate deviation which is caused by the difference of surface areas. Strips used in this test have constant weight and thickness and homogeneous surface, therefore deviation which is caused by the difference of surface areas can be eliminated.

Finally, in the results of the test about the fluidity of solution to remove the diffusion layer using the orbital water bath, there was no significant difference in the release pattern in the range of from 100 rpm to 200 rpm. And, because drug was released in perfect sink condition, the effect of fluidity of the solution on the release is negligible.

Analysis Instruments and Conditions

Analysis instrument: High Performance Liquid Chromatography [HPLC system: Beckman Co.]
Column: Reverse Phase [Spectra-Physics RP-8]
Mobile Phase: 0.2M Ammonium Oxalate:0.1M EDTA:DMF=550:200:250
Flow rate: 2 ml/min
Detector: UV-VIS Spectrophotometer, 280 nm
Injection volume: 20 μl
Kinetic Study Instrument: Orbital Water Bath and Clamp fitted for release equipment
Test temperature: 37° C.±0.5
Stock solution: Purified; water, 10 ml Release equipment: 30–50 ml shading equipment having height about 5 cm and open top covered with stopper to keep airtight state.

Solubility Measurement of Minocycline HCl

Into shading bottle, 500 mg of minocycline HCl was added with 10 ml of purified water. This mixture was maintained at 37° C. under stirring at 150 rpm in the orbital water bath. After 24 hours, this solution was taken by filtration and the concentration of minocycline in remained solution was measured using UV spectrophotometer. Each tripleted samples was tested three times and standard calibration curve was prepared using minocycline solution with 20 μg/ml, 40 μg/ml, 60 μg/ml and 100 μg/ml. The regression equation was Y=38.427X−2.189, and R, correlation coefficient, was 0.999377. Solubility of minocycline in water was 2.43 g with 0.02% deviation and test results are shown in Table 2.

TABLE 2

| | Solubility of minocycline HCl | | |
|---|---|---|---|
| the number of times | sample | concentration (μg/ml) | solubility | MEAN ± SE (%) |
| 1 | 1 | 47.69 | 2.38 | 2.41 ± 1.17 |
| | 2 | 47.96 | 2.40 | |
| | 3 | 49.00 | 2.45 | |
| 2 | 1 | 49.53 | 2.48 | 2.44 ± 1.25 |
| | 2 | 48.04 | 2.40 | |
| | 3 | 48.92 | 2.45 | |
| 3 | 1 | 49.50 | 2.48 | 2.44 ± 1.21 |
| | 2 | 48.07 | 2.49 | |
| | 3 | 48.96 | 2.40 | |
| | average | | | 2.43 ± 0.02 |

*dilution, 500 times

According to abovementioned kinetic study condition, release properties of strips prepared from the Examples and Comparative examples were examined and the results were studied about the release properties of minocycline according to composition of polymers, contents of minocycline and thickness of strips, and release property of minocycline in vitro. Also release property of minocycline in vitro to in vivo was studied. The results are shown as follows:

(i) Release Property of Minocycline Versus Composition of Polymers

Release properties of minocycline from strips prepared from the Examples 1 to 3 and Comparative example 1 were examined.

Figure 2:
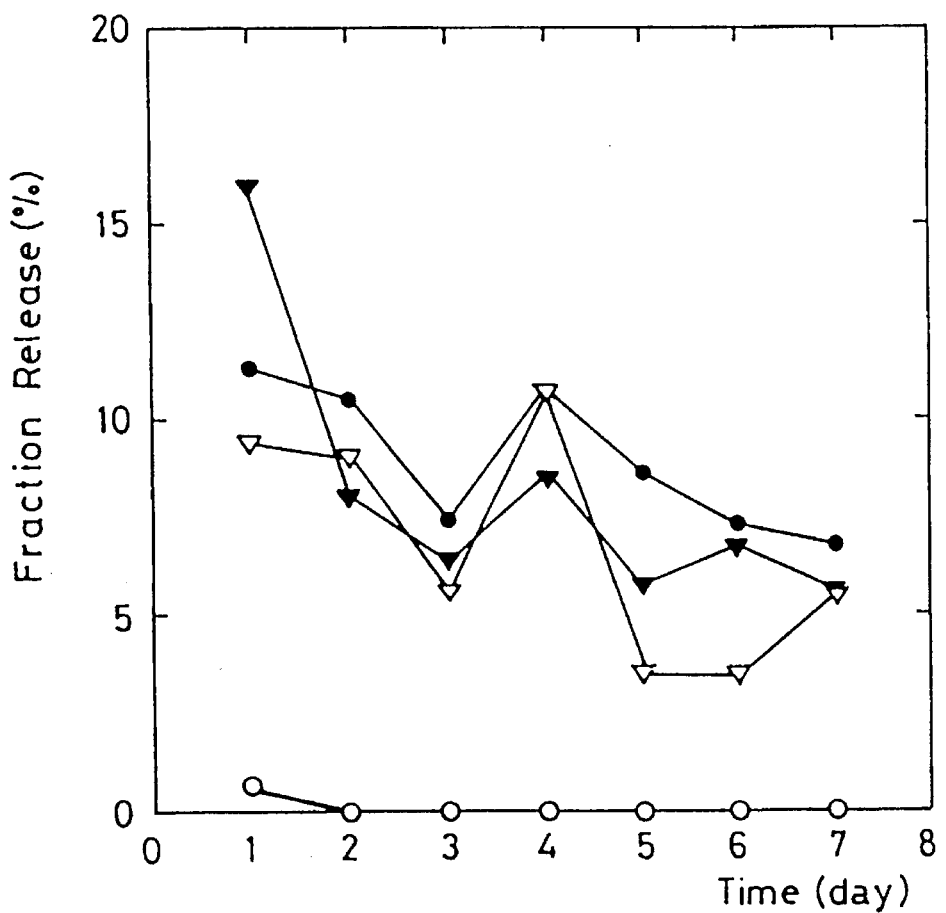
FIG. 2 is a graph representing the fraction release of minocycline of each strip-type local drug delivery film prepared from Examples 1 to 3 according to the present invention and Comparative example 1.
Figure 3:
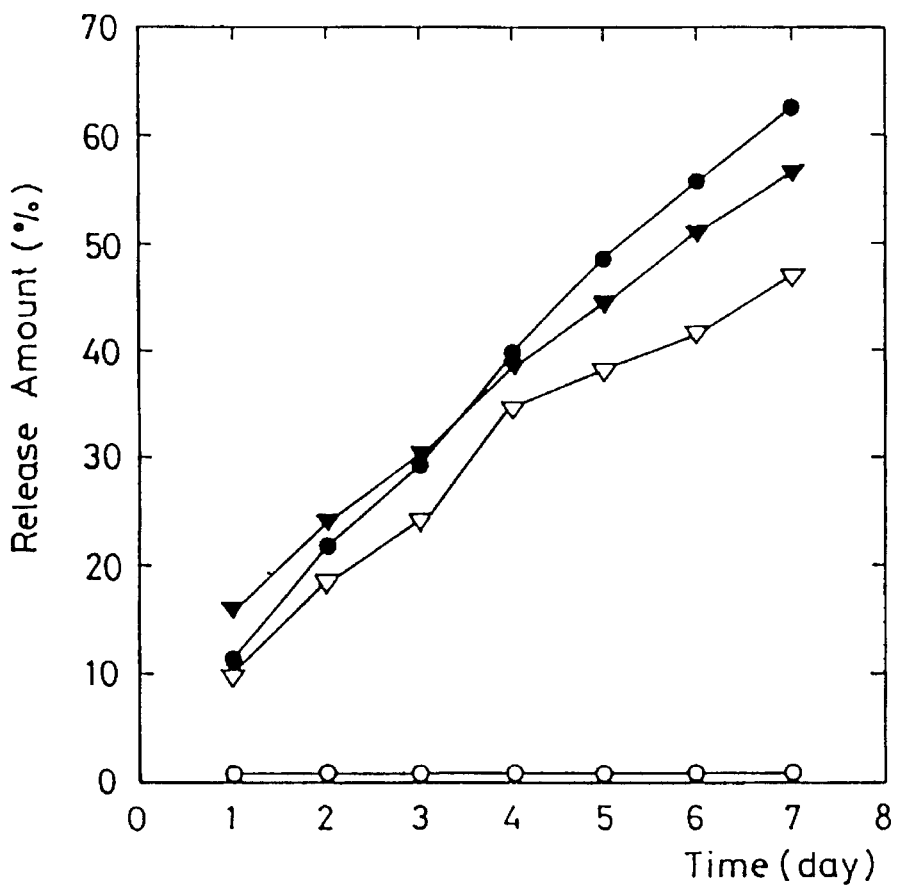
FIG. 3 is a graph representing the release amount of minocycline of each strip-type local drug delivery film prepared from Examples 1 to 3 according to the present invention and Comparative example 1.

According to the results of the measurement of release amount with the lapse of time for each strip, the strips prepared from Examples 1 to 3 showed the sustained release even after 7 days but the strip prepared from Comparative example 1 released only little amount of the minocycline at initial and did not show the sustained release. Results obtained are shown in table 3, FIG. 2 and FIG. 3.

Also, each strip was observed by scanning electron microscope before the release and after the release of minocycline. For the strip prepared from the Comparative example 1, pore was not observed on the surface of strip, but for the strips prepared from the Examples 1 to 3, many pores were observed on the surface of each strip. Thus, in the strip prepared from Comparative example 1, only minocycline exposed on the surface of the strip was dissolved into the solution, but in the strips prepared from the Examples 1 to 3 according to the present invention, minocycline was released from the inside of strip. Results obtained are shown in scanning electron microscope photographs of FIG. 9 to 12.

(ii) Release Property of Minocycline Versus Content of Minocycline

Strips prepared from Example 3 and Comparative examples 2 and 3 which have different minocycline contents respectively but have same thickness (200 μm) and same content ratio of polycaprolactone (1.5:1) were tested for the release properties of minocycline with the lapse of time. Results obtained are shown in Table 4 and FIG. 4 and 5.

Figure 4:
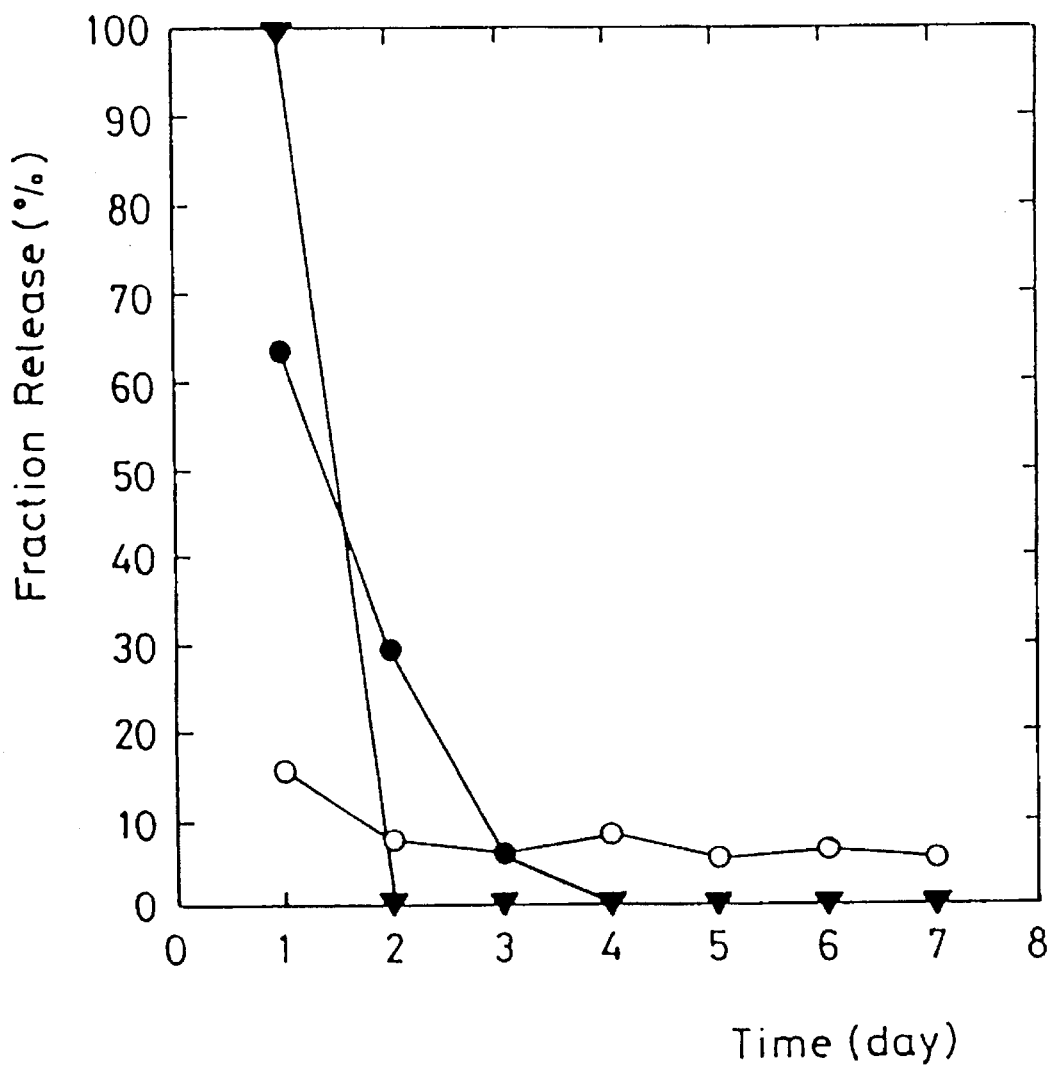
FIG. 4 is a graph representing the fraction release of minocycine of each strip-type local drug delivery film prepared from Example 3 according to the present invention and Comparative examples 2 and 3.
Figure 5:
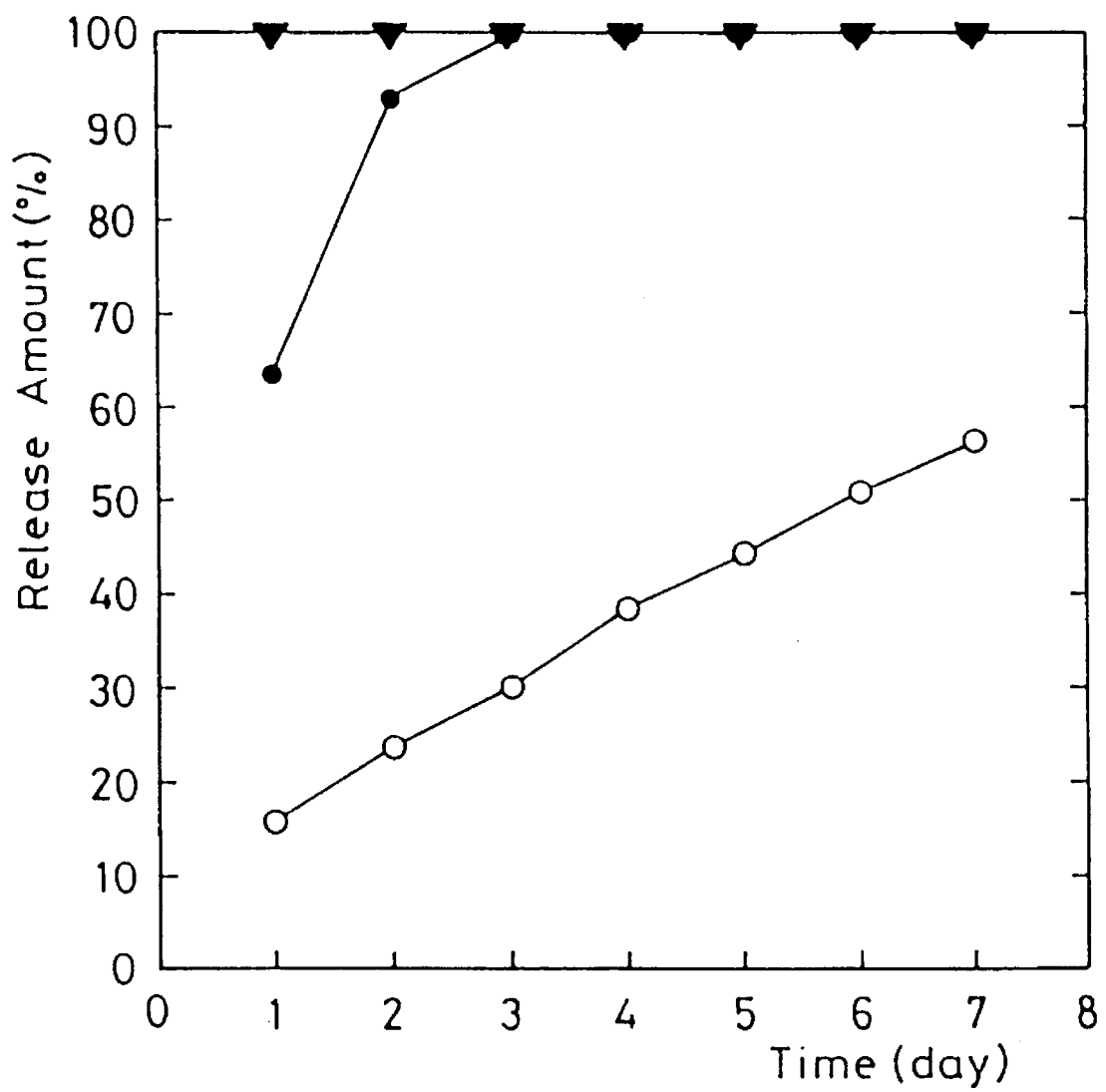
FIG. 5 is a graph representing the release amount of minocycline of each strip-type local drug delivery film prepared from Example 3 according to the present invention and Comparative examples 2 and 3.

As seen from Table 4 and FIG. 4 and 5, the local drug delivery strip containing 23% of minocycline (Example 3) showed desirable release pattern, but local drug delivery strips containing 40% of minocycline (Comparative example 2) and 30% of minocycline (Comparative example 3) showed undesirable release pattern.

(iii) Release Property of Minocycline Versus Thickness of Strip

Release properties of minocycline were tested in local drug delivery strips prepared from Examples 4 and 5 and Comparative example 3 which have same minocycline contents (30%) and same content ratio of polycaprolactons (1.5:1) but different thickness each other. Results obtained are shown in Table 5 and FIG. 6 and 7.

Figure 6:
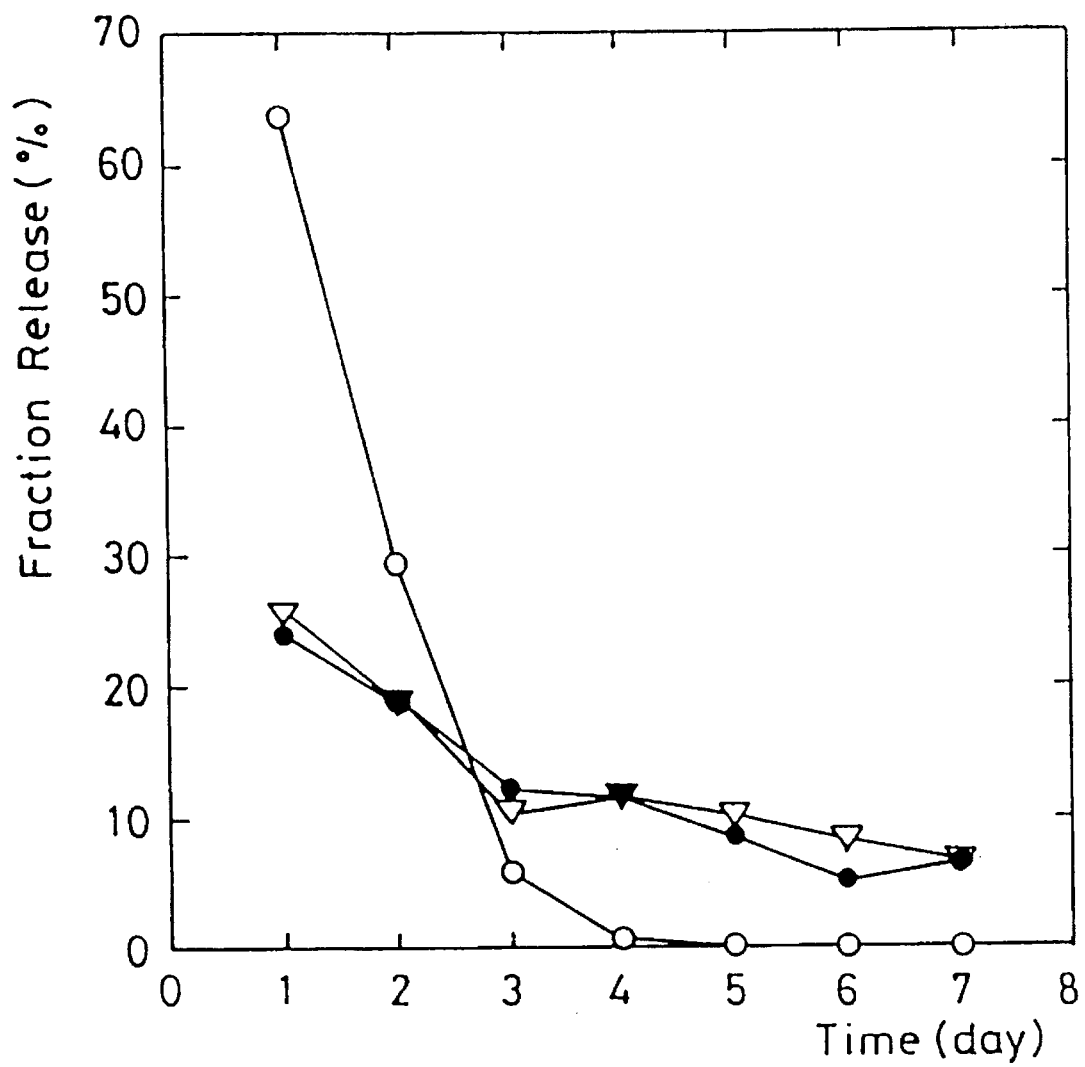
FIG. 6 is a graph representing the fraction release of minocycline of each strip-type local drug delivery film prepared from Examples 4 and 5 according to the present invention and Comparative example 3.
Figure 7:
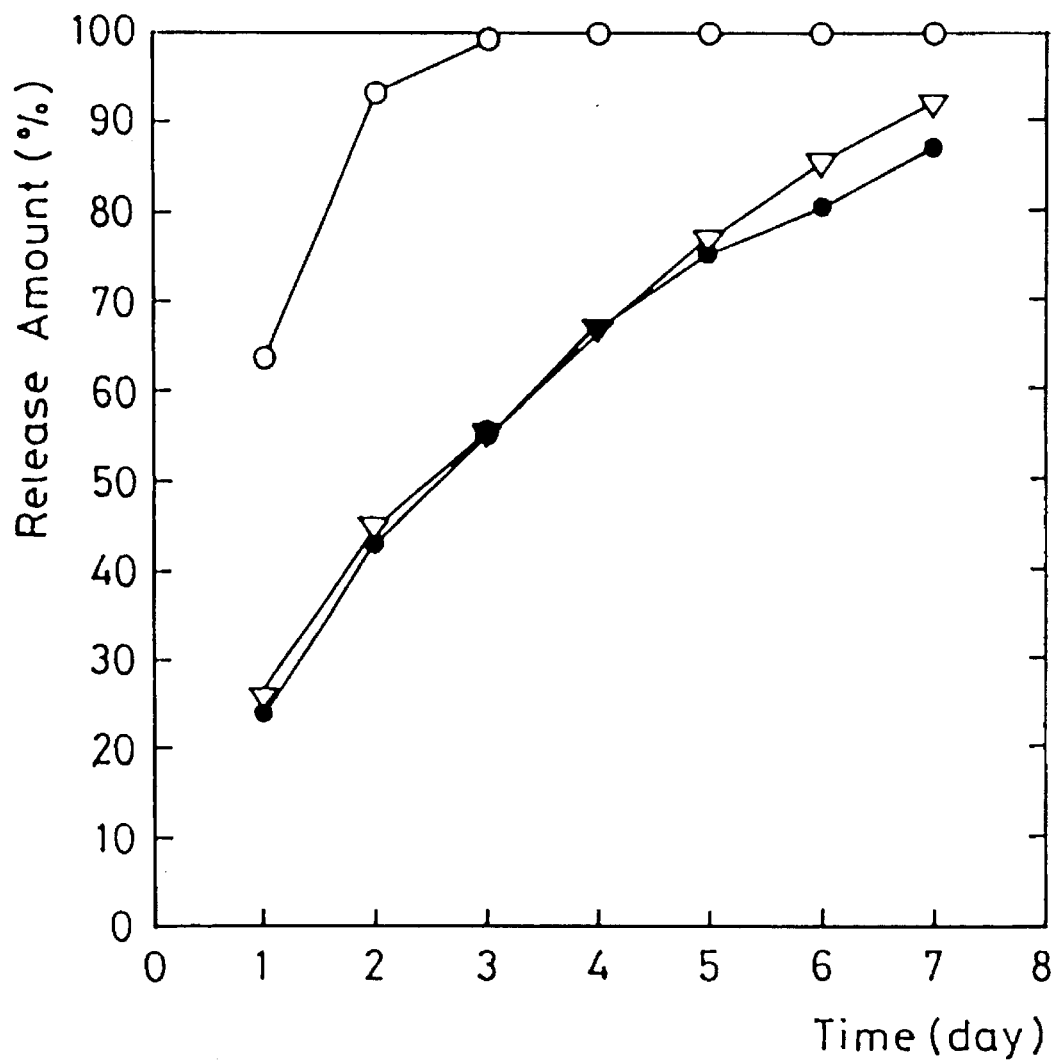
FIG. 7 is a graph representing the release amount of minocycline of each strip-type local drug delivery film prepared from Examples 4 and 5 according to the present invention and Comparative example 3.

As seen from Table 5 and FIG. 6 and 7, for local drug delivery strips containing 30% of minocycline, the strip of which thickness is 250 μm or 350 μm showed desirable release pattern, but the strip of which thickness is 200 um showed undesirable release pattern.

TABLE 3

| | Release of minocycline from local drug delivery strip (%) | | | | | | | |
|---|---|---|---|---|---|---|---|---|
| Time | Comparative Example 1 | | Example 1 | | Example 2 | | Example 3 | |
| (day) | Fraction | Amount | Fraction | Amount | Fraction | Amount | Fraction | Amount |
| 1 | 0.7 | 0.7 | 11.29 | 11.29 | 9.34 | 9.34 | 15.88 | 15.88 |
| 2 | 0.0 | 0.7 | 10.51 | 21.80 | 8.96 | 19.30 | 7.91 | 23.79 |
| 3 | 0.0 | 0.7 | 7.38 | 29.18 | 5.51 | 23.81 | 6.35 | 30.14 |
| 4 | 0.0 | 0.7 | 10.77 | 39.95 | 10.60 | 34.41 | 8.41 | 38.55 |
| 5 | 0.0 | 0.7 | 8.60 | 48.55 | 3.46 | 37.87 | 5.66 | 44.21 |
| 6 | 0.0 | 0.7 | 7.28 | 55.83 | 3.41 | 41.28 | 6.65 | 50.86 |
| 7 | 0.0 | 0.7 | 6.75 | 62.58 | 5.31 | 46.59 | 5.56 | 56.42 |

TABLE 4

Release of minocycline from local drug delivery strip, (%)

| Time (day) | Example 3 Fraction | Example 3 Amount | Comparative Example 3 Fraction | Comparative Example 3 Amount | Comparative Example 2 Fraction | Comparative Example 2 Amount |
|---|---|---|---|---|---|---|
| 1 | 15.88 | 15.88 | 63.64 | 63.64 | 99.18 | 99.18 |
| 2 | 7.91 | 23.79 | 29.47 | 93.11 | 0.32 | 99.50 |
| 3 | 6.35 | 30.14 | 5.92 | 99.03 | 0.00 | 99.50 |
| 4 | 8.41 | 38.55 | 0.63 | 99.66 | 0.00 | 99.50 |
| 5 | 5.66 | 44.21 | 0.21 | 99.78 | 0.00 | 99.50 |
| 6 | 6.65 | 50.86 | 0.00 | 99.78 | 0.00 | 99.50 |
| 7 | 5.56 | 56.42 | 0.00 | 99.78 | 0.00 | 99.50 |

TABLE 5

Release of minocycline from local drug delivery strip, (%)

| Time (day) | Comparative Example 3 Fraction | Comparative Example 3 Amount | Example 4 Fraction | Example 4 Amount | Example 5 Fraction | Example 5 Amount |
|---|---|---|---|---|---|---|
| 1 | 63.64 | 63.63 | 23.97 | 23.97 | 25.63 | 25.63 |
| 2 | 29.47 | 93.11 | 18.88 | 42.85 | 18.88 | 44.51 |
| 3 | 5.92 | 99.03 | 12.48 | 55.33 | 10.44 | 54.95 |
| 4 | 0.63 | 99.66 | 11.49 | 66.82 | 11.58 | 66.53 |
| 5 | 0.12 | 99.78 | 8.63 | 75.45 | 10.18 | 76.71 |
| 6 | 0.00 | 99.78 | 5.15 | 80.06 | 8.28 | 84.99 |
| 7 | — | — | 6.42 | 87.02 | 6.59 | 91.58 |
| 8 | — | — | 3.9 | 90.92 | 3.68 | 95.44 |
| 9 | — | — | 2.29 | 93.21 | 2.19 | 97.63 |

(iv) Release Properties of Minocycline In Vitro and In Vivo

To use for quality control, in vitro release pattern of the local drug delivery strip obtained from Example 6 was tested by the method designed according to Film Theory of Dissolution.

As a results, release rate of minocycline after 1 hour was 72.8 μg/35 mm$^2$/hr which showed initial burst effect and then release rate became decrease after 3 hours and more than 90% of minocycline was released with release rate of 4–5 μg/35 mm$^2$/hr at 6 or 7 days. At this time, half life of release was about 3 days.

Also, as shown in Table 7, release amount after 6 days is 5.96% of content, that is 101.3 μg which can keep the concentration as much as 422.1 μg/ml at applying position when gingival fluid flow is regarded as 10 μl/hr. This is effective release concentration of drug over the theoretical effective concentration, 2–4 μg/ml, and if accumulation of drug itself is considered, more than said concentration can be expected and it can be proved by 899 μg/ml which was obtained in vivo release test mentioned hereinafter.

That is, it can be expected that the concentration of drug at applying position be kept with effective concentration for periodontal treatment because the local drug delivery strip showed release pattern with designated standard.

In this study, the local drug delivery strip was inserted into periodontal pocket and the concentration of minocycline in periodontal pocket was measured. The results of in vivo release study of monocycline using 10 strips prepared from Example 6 are shown in Table 6.

Because of initial burst effect, minocycline concentration in periodontal pocket was 1,363 μg/ml after 1 hour and 1,500 μg/ml after 2 hours, which was maximum concentration. After 7 days, minocycline concentration in periodontal pocket was 89 μg/ml. In this study, half life of release was 7.8 days which showed excellent sustained release pattern.

That is, the local drug delivery strip according to present invention is effective for periodontal treatment as which is applied into periodontal pocket which is impacted position and wherein effective concentration to sterilize bacilli is sustained for at least 7 days.

Result of in vivo test are shown in Table 6 and release pattern is represented as equation $Y=-97.28X+1490$ and correlation coefficient, R, is 0.850.

Figure 8:
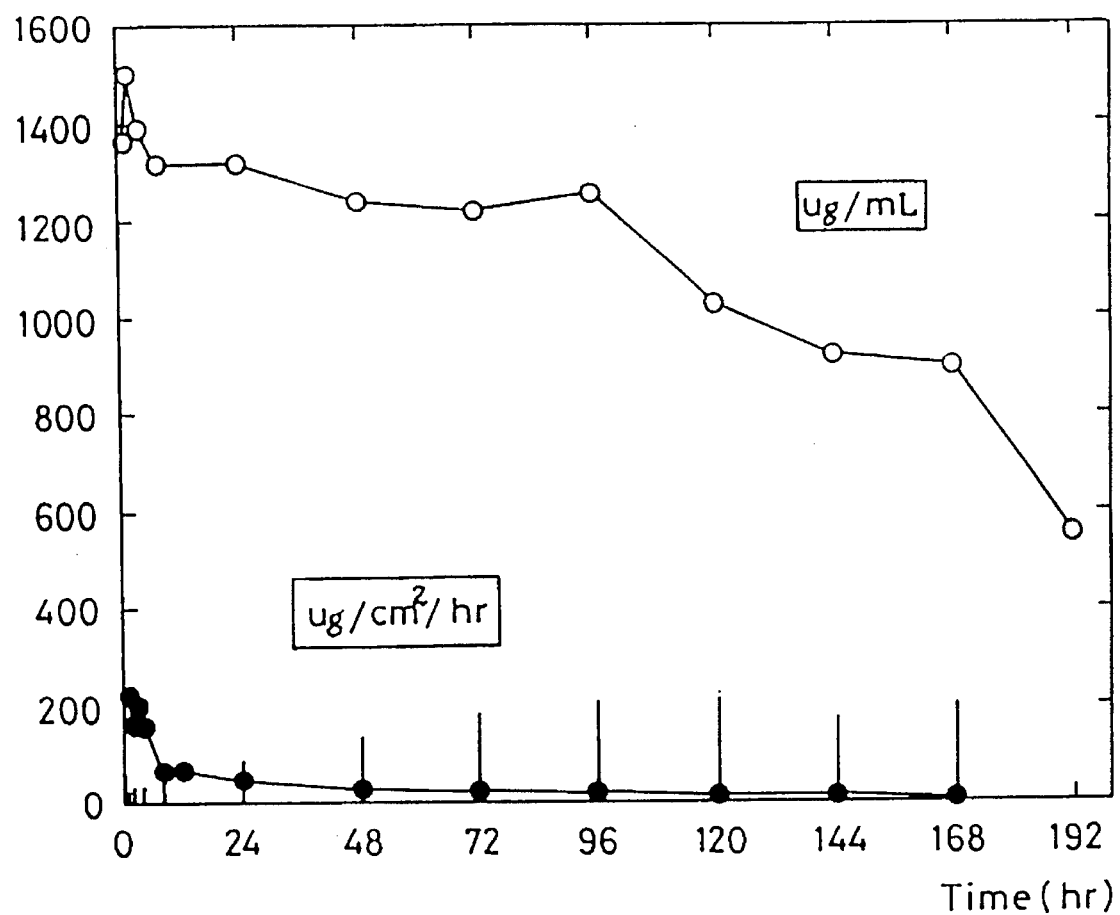
FIG. 8 is a graph representing the release rate of minocycline in vitro and the concentration of minocycline in vivo of the strip-type local drug delivery film prepared from Example 8 according to the present invention.
Figure 9A:
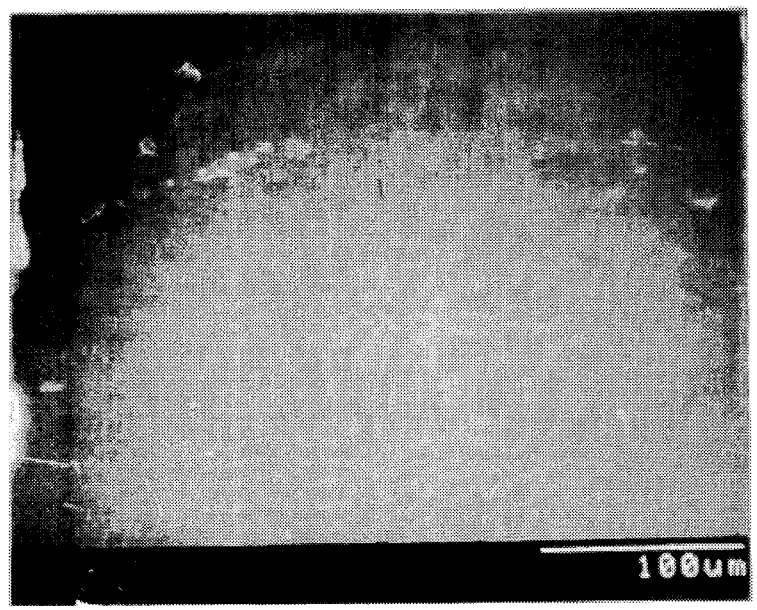
FIGS. 9A and 9B are scanning electron microscope photographs representing before release and after release for 7 days of minocycline of the strip-type local drug delivery film prepared from Comparative example 1 respectively.
Figure 9B:
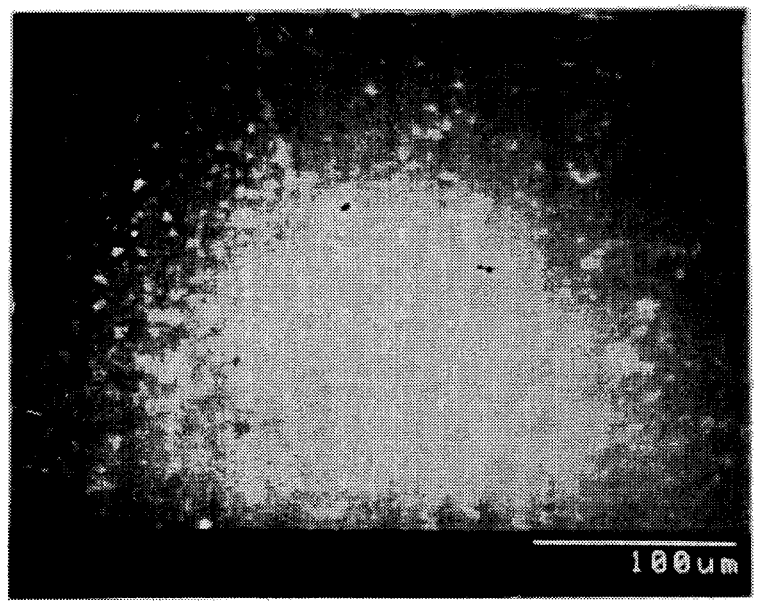
Figure 10A:
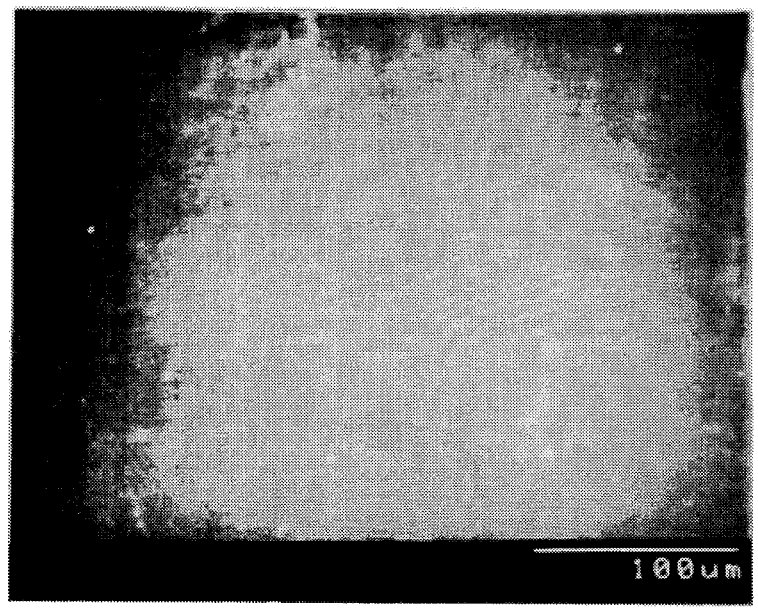
FIGS. 10A and 10B are scanning electron microscope photographs representing before release and after release for 7 days of minocycline of the strip-type local drug delivery film prepared from Example 1 according to the present invention respectively.
Figure 10B:
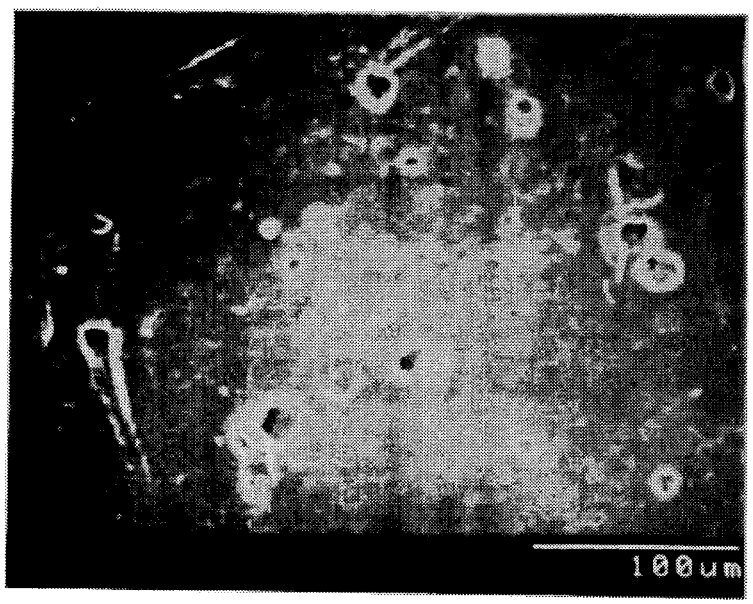
Figure 12A:
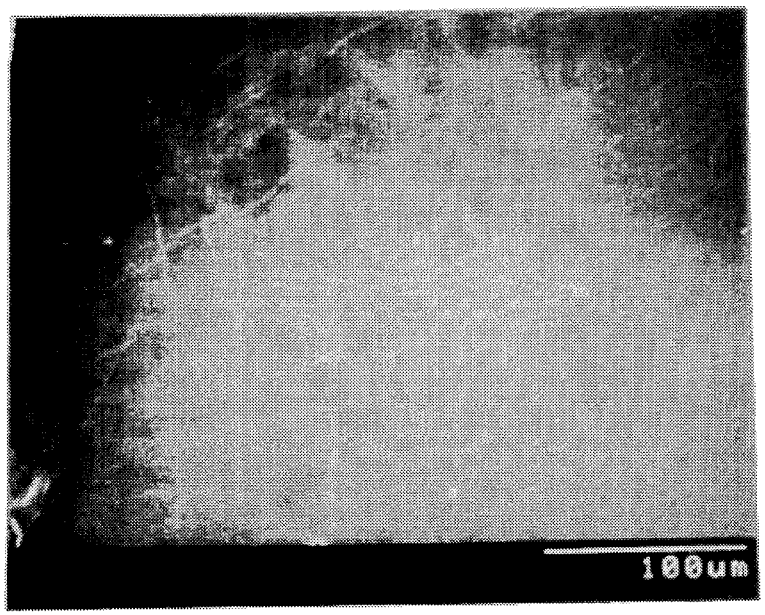
FIGS. 12A and 12B are scanning electron microscope photographs representing before release and after release for 7 days of minocycline of the strip-type local drug delivery film prepared from Example 3 according to the present invention respectively.
Figure 12B:
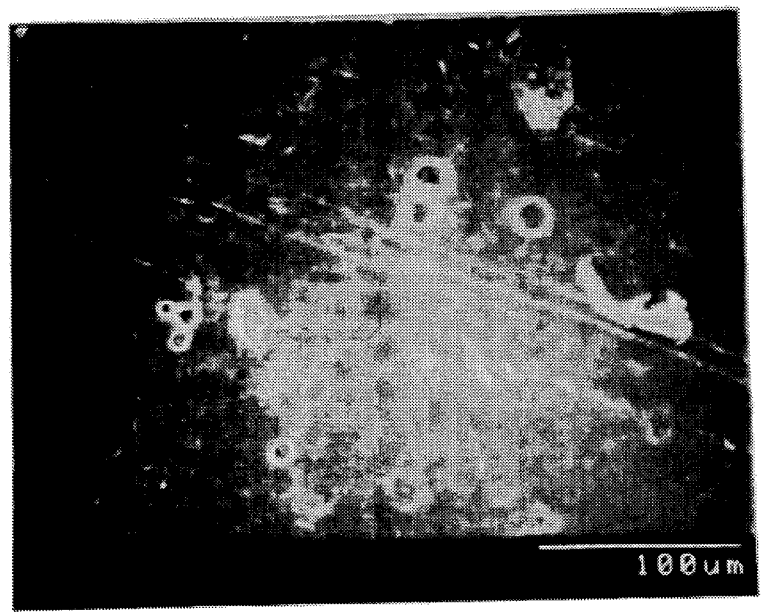

From the in vivo test of the local drug delivery strip, minocycline concentration in periodontal pocket is higher than that in vitro test. It is considered due to accumulation of minocycline in periodontal pocket. The results of release test in vitro and in vivo are shown in Table 6 and 7 and FIG. 8.

TABLE 6

In vivo concentration of released minocycline from local drug delivery strip in the periodontal pocket

| hr | ① | ② | ③ | ④ | ⑤ | ⑥ | ⑦ | ⑧ | ⑨ | ⑩ | MEAN ± SD | Conc. of MC |
|---|---|---|---|---|---|---|---|---|---|---|---|---|
| 1 | 2.9 | 2.8 | 2.8 | 2.9 | 2.8 | 2.8 | 2.6 | 2.6 | 2.5 | 2.7 | 2.74 ± 0.438 | 1363 |
| 2 | 2.9 | 2.9 | 2.9 | 2.9 | 3.1 | 2.8 | 2.9 | 3.0 | 2.8 | 2.8 | 2.90 ± 0.462 | 1500 |
| 4 | 2.6 | 2.9 | 2.9 | 2.5 | 2.8 | 2.8 | 2.9 | 2.8 | 2.7 | 2.8 | 2.77 ± 0.442 | 1390 |
| 8 | 2.7 | 3.0 | 2.7 | 2.7 | 2.9 | 2.5 | 2.7 | 2.5 | 2.6 | 2.7 | 2.70 ± 0.431 | 1328 |
| 24 | 2.9 | 2.8 | 2.9 | 2.7 | 3.1 | 2.7 | 2.6 | 2.6 | 2.6 | 2.0 | 2.69 ± 0.430 | 1319 |
| 48 | 2.5 | 2.8 | 2.7 | 2.0 | 3.0 | 2.7 | 2.8 | 2.3 | 2.7 | 2.5 | 2.60 ± 0.415 | 1237 |
| 72 | 2.0 | 2.7 | 2.7 | 2.7 | 2.6 | 2.6 | 2.6 | 2.7 | 2.6 | 2.6 | 2.58 ± 0.412 | 1218 |
| 96 | 2.6 | 2.7 | 2.7 | 2.6 | 2.7 | 2.4 | — | — | — | — | 2.62 ± 0.418 | 1252 |
| 120 | 2.3 | 2.3 | 2.2 | 2.4 | 2.5 | — | 2.5 | 2.3 | 2.4 | 2.5 | 2.38 ± 0.376 | 1022 |
| 144 | — | — | — | — | — | 2.4 | 2.3 | 2.2 | 2.1 | 2.4 | 2.28 ± 0.358 | 920 |
| 168 | 2.2 | 2.2 | 2.7 | 2.2 | 2.4 | 2.3 | 2.1 | 2.2 | 2.2 | 2.1 | 2.26 ± 0.354 | 899 |
| 192 | 2.2 | 2.0 | 1.9 | 2.1 | 2.1 | 2.4 | 1.7 | 1.7 | 1.8 | 1.6 | 1.96 ± 0.292 | 553 | standard error of X coefficient: 16.1596
standard error of Y Est.: 104.7259
—: non detectable

TABLE 7

Comparison of in vivo and in vitro release rate of local drug delivery

| Time (hr) | In vivo Conc of MC (μg/ml) (B) | In vitro release rate (μg/35 mm²/hr) (A) | (μg/cm²/hr) | fraction (%) | amount (%) | C(= B/A) |
|---|---|---|---|---|---|---|
| 1 | 1,363 | 72.8 | 225.8 | 4.26 | 4.26 | 18.7 |
| 2 | 1,500 | 52.8 | 163.8 | 3.09 | 7.35 | 28.4 |
| 3 | — | 64.6 | 200.4 | 3.78 | 11.13 | — |
| 4 | 1,390 | 51.3 | 159.0 | 3.00 | 14.13 | 27.1 |
| 8 | 1,320 | 20.5 | 63.5 | 4.79 | 18.92 | 64.4 |
| 12 | — | 22.1 | 68.4 | 5.16 | 24.08 | — |
| 24 | 1,319 | 15.1 | 46.7 | 10.58 | 34.66 | 87.6 |
| 48 | 1,237 | 8.7 | 27.0 | 12.22 | 46.88 | 142.0 |
| 72 | 1,218 | 6.6 | 20.6 | 9.31 | 56.19 | 183.3 |
| 96 | 1,252 | 6.0 | 18.7 | 8.46 | 64.65 | 207.3 |
| 120 | 1,022 | 4.5 | 14.0 | 6.33 | 70.98 | 226.3 |
| 144 | 920 | 5.2 | 16.0 | 7.24 | 78.22 | 178.3 |
| 168 | 899 | 4.3 | 13.2 | 5.96 | 84.18 | 211.1 |
| 192 | 553 | — | — | — | — | — |

Cytotoxic Test of Local Drug Delivery Strip

Local drug delivery strip obtained from Example 6 was examined about following properties:
(i) Cytotoxic Inhibition Activity in Human Gingival Fibroblast Human gingival fibroblast was cultivated and divided into 24 multi-well dish as much as 1×10⁵ cell/well each. Medium was chant ed next day. After 3 days, medium was removed and washed with Hank's balanced salt solution (hereinafter it is abbreviated to HBSS). Washed gingival fibroblast was incubated for 48 hours in medium containing the strip obtained from Example 6, in medium containing only minocyclin as control, and in minimum essential medium (hereinafter it is abbreviated to MEM) respectively, and added [$^3$H]-thimidine 5 μCi into each well. After 2 hours, said solutions were stood at 4° C. for 10 min using ice cold 5% Trichloroacetic acid (TCA) 3 ml. After washing 3 or 4 times with TCA, removed TCA, and dissolved gingival fibroblast by 0.5N-NaOH 1 ml at 37° C. for 30 min. 50 μl of said solution was taken, added 4 ml of cocktail solution to said solution and count per minute was measured by liquid scintillation counter. Measured results are shown in Table 8. Table 8 showed result measured according to release amount of minocycline.

As shown Table 8, there was no any statistical significance to the concentration of minocycline and growth inhibitor of gingival fibroblast with the lapse of time.
(ii) Rapid Colorimetric Assay for Cellular Growth Survival Incubated human gingival fibroblast was treated with 0.25% trypsin-EDTA solution and centrifuged. The floating solution obtained was devided into microtest plate well (obtained from Nuck, Denmark) as much as 2.5×10 cell/well using the standard blood corpuscle calculation method so that MEM containing 10% fatal calf serum, peniciline 10 units/ml, streptomycine 100 μg/ml and fungizone 0.2 μl/ml became containing 2500, 5000, 10000, 15000, 20000, and 30000 cell per 200 ml and the resulting solution was incubated. Culture solution was changed next day. After 2 days, culture solution was removed and washed with HBSS. 200 ml of culture solution containing the strip obtained from Example 6 was added in each well. This was incubated in incubator at 37° C. 5% $CO_2$ and humidity 100% for 24 hours and 50 μl of 3-(4,5-dimethyl thiazol-2-YL)-2,5-diphenyl tetrazolium bromide [MTT: Sigma, U.S.A.] which was dissolved in Isotonic salt solution was added into each well, incubated for 4 hours, poured out the MTT solution and added DMSO 50 μl into each well to dissolve the formazon crystal. MTT inspection was carried out to measure the extent of growth of cell with incubating the solution in incubator at 37° C., 5% $CO_2$ using ELISA reader(Bio-teck Instruments Inc., Model EL 308) at 570 nm. As control group, MEM culture solution well was used every test. All test results were calculated as percentage unit to control group. Obtained results are shown in Table 9. As seen in Table 9, in the activity test using the human gingival fibroblast, difference in cell activity according to the minocycline concentration was not observed.

TABLE 8

Cell cytotoxic study of local drug delivery according to the amount of released sample, (count per minute of [$^3$H] incorporation)

| | Mean ± SE |
|---|---|
| α-MEM | 1995.0 ± 655.0 |
| Control | 2377.5 ± 308.7 |
| 160 μg | 1900.0 ± 170.0 |
| 320 μg | 1755.0 ± 505.0 |
| 640 μg | 1670.0 ± 650.0 |
| 1280 μg | 1460.0 ± 410.0 |
| 2560 μg | 1360.0 ± 380.0* |

*statistically significant (P < 0.05)

TABLE 9

Cell growth survival according to the concentration of local 30% minocycline delivery

| sample | concentration (μg/ml) | cell viability (%) |
|---|---|---|
| α-MEM | 0 | 99.50 ± 4.00 |
| 70% Ethanol | 0 | 100.00 ± 10.61 |
| Minocycline | 160 | 121.25 ± 15.00 |
| Minocycline | 640 | 110.63 ± 6.70 |
| Minocycline | 2560 | 109.38 ± 5.63 |

As seen in Table 8 and 9 above mentioned, at the concentration of minocycline in the range of from 160 μg/ml to 2560 μg/ml which was provided from the experimental condition, growth of gingival fibroblast was not inhibited and even in the results of observation for 7 days statistical singnificance about growth inhibitory of gingival fibroblast was not observed.

Also, in the test using human gingival fibroblast the difference in cell activity according to concentration of minocycline was not observed. Relating to the increase of DNA synthesis, it is difficult to observe significant difference in the formation of gingival fibroblast and cell activity. It proves that the local drug delivery according to the present invention is stable for clinical use.

According to the present invention forementioned, the local drug delivery film which provides the effective antibiotic effect by sustained release of the drug for a long time and can be expected to provide excellent treatment effect with one tenth of the conventional prescription amount for adults and can be prepared by melt casting method. This solved problems about stability for application in the human body caused by remaining poisonous solvent and about the nonhomgeneous release of drug due to uneven distribution of the drug causing uneven volatility of solvent during the preparation of the local drug delivery film, and by which quality control can be done easily and the cost of preparation can be brought down.

What is claimed is:

1. A local drug delivery film for periodontal treatment containing a release component and an active component consisting of,
    (a) as release component, 60% to 90% by total weight of drug delivery film of polymer mixture of polycaprolactone I having number average molecular weight in a range of from 30,000 to 60,000 and polycaprolactone II having number average molecular weight less than 1,000, the content ratio of the polycaprolactone I to polycaprolactone II being from 1:1 to 4:1, and
    (b) as active component, 10% to 40% by total weight of drug delivery film of periodontal therapeutic agent.

2. The local drug delivery film according to claim 1, wherein said molecular weight of polycaprolactone II is in the range of from 860 to 1000.

3. The local drug delivery film according to claim 1 wherein said ratio of polycaprolactone I to polycaprolactone II is in the range of 1.5:1–3:1.

4. A local drug delivery film according to claim 1, wherein said active component is at least one kind of antibiotic selected from the group consisting of minocycline, tetracycline, doxycycline, chlorohexidine, clindamycin, orfloxacin, metronidazole, tinidazole and ketoconazole.

5. The local drug delivery film according to claim 1, wherein said content of active component is in the range of 23% to 30% by total weight of drug delivery film.

6. The local drug delivery film according to claim 1, wherein the thickness of film is in the range of from 100 μm to 400 μm.

7. The local drug delivery film according to claim 6, wherein the thickness of film is in the range of from 200 μm to 350 μm.

8. A method for preparing a local drug delivery film for periodontal treatment containing a release component and an active component consisting of the steps of,
    (a) mixing in melt state the release component having 60% to 90% by total weight of drug delivery film of polymer mixture of polycaprolactone I having number average molecular weight in a range of from 30,000 to 60,000 and polycaprolactone II having number average molecular weight less than 1,000, the content ratio of polycaprolactone I to polycaprolactone II being from 1:1 to 4:1 with the active component having 10% to 40% by total weight of drug delivery film of periodontal therapeutic agent; and
    (b) melt-pressing said release and active components into the drug delivery film.

9. The local drug delivery film according to claim 1, wherein said local drug delivery film further consists of at least one corner on the film, said corner of the film being rounded off and the middle of the film being narrow relative to the film ends.

10. A method according to claim 8 wherein said melt-pressing step further consists of a melt-extrusion step.

11. A method according to claim 8 for preparing a local drug delivery film consisting of the further steps of rounding off the corners of the film and narrowing the film middle relative to the film ends.

* * * * *